(12) United States Patent
Gammons et al.

(10) Patent No.: US 6,699,270 B2
(45) Date of Patent: Mar. 2, 2004

(54) CONVECTIVE HEAT THERAPY DEVICE EXHAUST PORTS

(75) Inventors: Clifford E. Gammons, Loudon, TN (US); Joseph G. Jones, Englewood, TN (US)

(73) Assignee: Adroit Development, Inc., Loudon, TN (US)

( * ) Notice: Subject to any disclaimer, the term of this patent is extended or adjusted under 35 U.S.C. 154(b) by 0 days.

(21) Appl. No.: 10/126,716

(22) Filed: Apr. 19, 2002

(65) Prior Publication Data

US 2003/0023292 A1 Jan. 30, 2003

Related U.S. Application Data

(63) Continuation-in-part of application No. 09/916,353, filed on Jul. 27, 2001.

(51) Int. Cl.[7] .................................................. A61F 7/00
(52) U.S. Cl. ...................................... 607/107; 607/109
(58) Field of Search ................................ 607/107, 109

(56) References Cited

U.S. PATENT DOCUMENTS

| | | | | |
|---|---|---|---|---|
| 4,572,188 A | * | 2/1986 | Augustine et al. | 607/107 |
| 5,165,400 A | * | 11/1992 | Berke | 607/104 |
| 5,246,656 A | * | 9/1993 | Stephenson et al. | 264/153 |
| 5,300,101 A | | 4/1994 | Augustine et al. | |
| 5,443,488 A | * | 8/1995 | Namenye et al. | 607/104 |
| 5,674,269 A | * | 10/1997 | Augustine | 607/107 |

* cited by examiner

*Primary Examiner*—Roy D. Gibson
(74) *Attorney, Agent, or Firm*—Pitts & Brittian PC (57) ABSTRACT

A therapy device for providing heated air to the body of a patient through a plurality of V-shaped slits. The therapy device is an inflatable tube. A heated air supply is connected to the tube and the heated air inflates the tube and is forced out of the exhaust ports. The exhaust ports are V-shaped slits. The method of fabricating the therapy device includes forming the individual pieces, attaching the tube sheets to form a tube, lancing the tube to form exhaust ports, and attaching the remaining pieces.

8 Claims, 13 Drawing Sheets

CONVECTIVE HEAT THERAPY DEVICE EXHAUST PORTS

CROSS-REFERENCE TO RELATED APPLICATIONS

This application is a Continuation-In-Part of Ser. No. 09/916,353, filed on Jul. 27, 2001.

STATEMENT REGARDING FEDERALLY SPONSORED RESEARCH OR DEVELOPMENT

Not Applicable

BACKGROUND OF THE INVENTION

1. Field of Invention

This invention relates to the field of heat therapy. More specifically, the present invention relates to the exhaust ports formed in a disposable hypothermia article used to supply a source of controlled temperature air to a patient's upper body surface.

2. Description of the Related Art

During and after a surgical procedure, it is well known that the loss of body temperature by the patient can lead to hypothermia. Accordingly, it is well known to apply heat to the patient in order to replace the heat that is lost. While heat loss associated with surgery is discussed herein, it is well known that hypothermia is also caused by other circumstances, such as prolonged exposure to extreme cold. No matter what the cause of hypothermia, it is essential to apply heat to the patient in order to either prevent or overcome hypothermia.

One method for applying heat to a patient is by directing warm air toward the patient. Of specific interest is a generally U-shaped hollow tubular member through which heated air is supplied. Typical of the art are those devices disclosed is U.S. Pat. No. 5,165,400, titled "Convective Hyperthermia Article," issued to Berke on Nov. 24, 1992; and U.S. Pat. No. 5,300,101, titled "Method and Apparatus for Treatment of Pediatric Hypothermia," issued to Augustine, et al., on Apr. 5, 1994.

The '400 device disclosed by Berke is a U-shaped device having two substantially parallel legs positioned adjacent to and extending a substantial length of a patient's body. The '400 device has a tubular cross-piece connecting the two legs, through which heated air is directed by a heat source. The '400 device includes an upper layer of material and a lower layer of material that are joined together at fold lines along side seams to provide a tubular leg through which heated air is directed. Through the inner surface area of the legs and the cross-piece, a multitude of discrete, uniformly spaced, air holes are punched entirely through the upper and lower layers of material along a side seam for flow of heated air through each discrete air hole. Each air hole provides a stream of heated air that is ejected from each hole at a rate depending on the diameter of each hole and the rate of pumping of the heated air through each tubular leg.

The '101 device disclosed by Augustine is a device similar to that disclosed in the '400 patent, except that the device fits an infant or small child and includes coverings that are attachable along the length of the inflatable body. The device includes a multitude of apertures for the ejection of air, with the apertures extending entirely through an underside layer and an upper layer of material having a stratum of absorbent tissue paper prelaminated with a layer of heat-sealable plastic bonded thereto.

BRIEF SUMMARY OF THE INVENTION

The therapy device exhausts heated air towards the patient through orifices, or exhaust ports, in the therapy device. The orifices are slits cut into the wall of the therapy device at locations where the exhausting air will be directed towards the patient. In one embodiment, the slits are v-shaped cuts with the v-shaped cut aimed in the direction of a circumference of the inflated therapy device.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
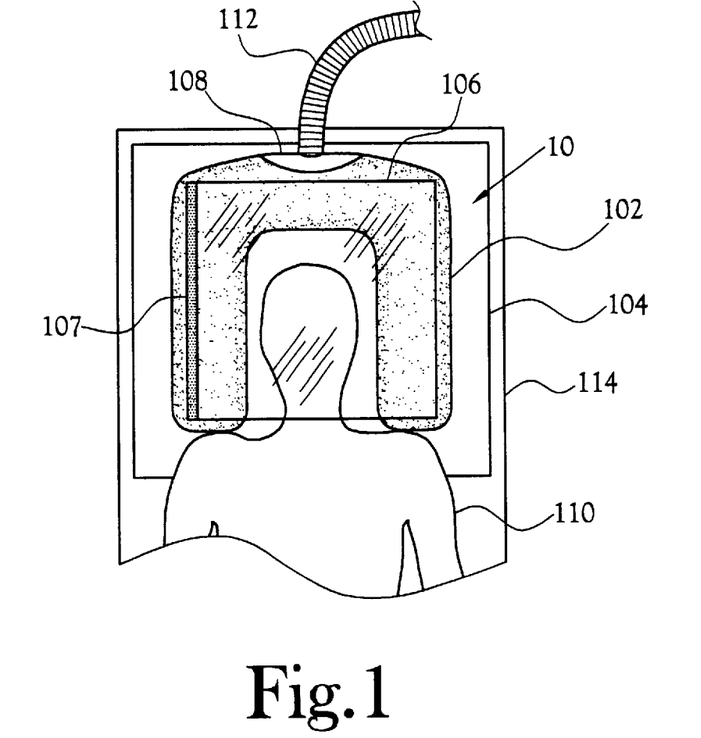
FIG. 1 is a top view of a patient with the therapy device inflated and in place.

An apparatus for a convective heat therapy device and a method of making and using the device is disclosed. The therapy device is generally referred to in the figures as item 10, 910, 1010, 1110, and 1410. Referring to FIG. 1, one embodiment of the therapy device 10 provides warm air to the upper portion of a patient's body 110. A base sheet 104 is placed under the head and shoulders of the patient 110, who is lying on a table or bed 114. The therapy device 10 is connected to a supply hose 112 from a heated air supply (not illustrated). When air is pumped into the therapy device 10, the tube 102 inflates, and heated air is exhausted in a thermal warming zone surrounding a portion of the patient's body 110. A cover sheet 106 prevents the heated air from immediately escaping and is attached 107 to one leg of the tube 102. The cover sheet 106 is positioned over the head of the patient 110 and placed on top of the tube 102.

Figure 2:
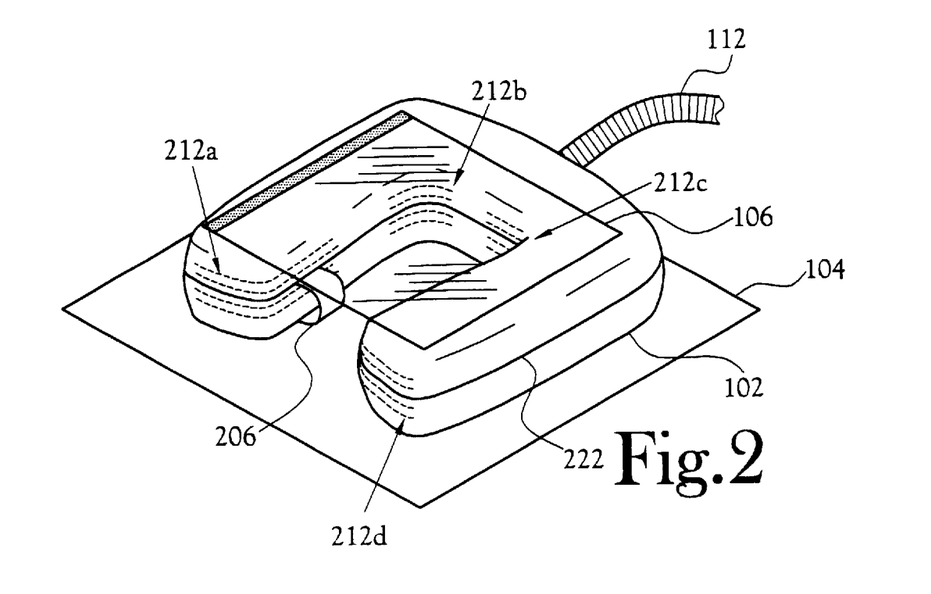
FIG. 2 is a perspective view of the therapy device.

FIG. 2 illustrates a perspective view of an inflated therapy device 10. A first securing strap 206 extending from the seam 222 on the inside of the tube 102 is attached to the base sheet 104. A second securing strap 306 (not illustrated in FIG. 2) extends similarly from the seam opposite that of the first securing strap 206. The securing straps 206, 306 are attached to the base sheet 104 by any of various methods known by those skilled in the art, including welding, double-sided tape, or hot-glue.

The cover sheet 106 is a clear plastic material that forms a tent over the head of the patient 110 and serves to direct the escaping air over a greater portion of the body of the patient 110 by preventing the immediate escape of the heated air. A portion of one end 107 of the cover sheet 106 is attached 107 to one leg of the tube 102 using means known to those skilled in the art, for example, welding, double-sided tape, or hot-glue.

Figure 12:
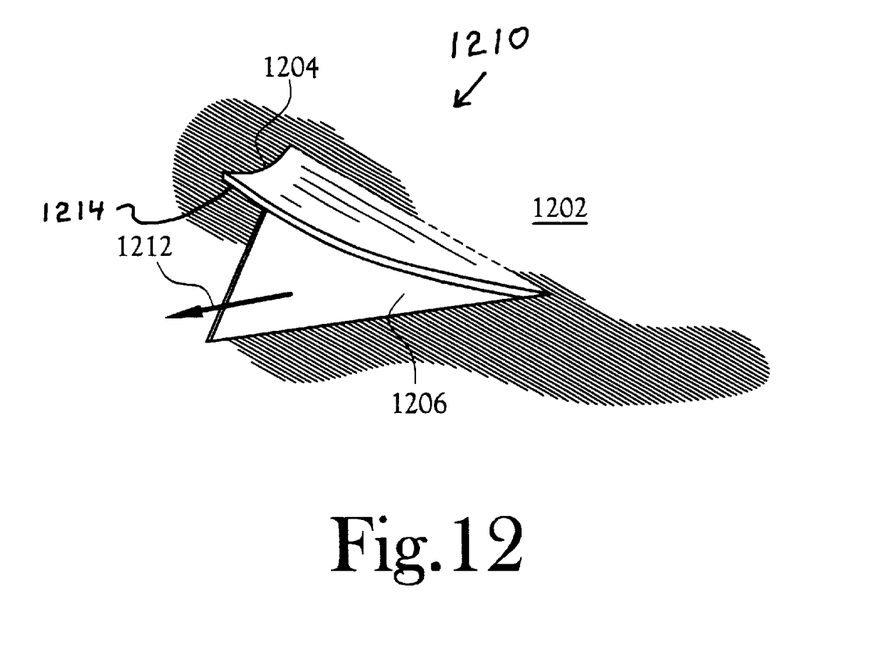
FIG. 12 is a perspective view of a straight slit.

Also shown in FIG. 2 are the exhaust ports 212a, 212b, 212c, 212d through which the heated air forced into the therapy device 10 escapes. The slits 1310 are substantially parallel to a line tangent to the nearest seam edge of the tube 102. Alternatively, the slits 1310 are substantially perpendicular to the tangent of a circumference of the tube 102 defined by a radius perpendicular to the axis of the tube 102, that is, the length of the slit 1310 follows the longitudinal axis of the tube 102. Although FIG. 2 illustrates straight slits 1310, in another embodiment, the exhaust ports 212 are V-shaped slits 1210, as illustrated in FIG. 12; that is, each exhaust port 212 is formed of two slits that are connected at one end and separated at the other end. In still another embodiment, the exhaust ports 212 are holes cut or punched into the tube 102.

In yet another embodiment, the exhaust ports 212 are an integral part of the fabric of the tube 102. That is, the tube 102 is fabricated with material that is air impermeable in all areas except where the exhaust ports 212 are located. For example, the tube 102 is fabricated out of air permeable fabric that is coated with a thin sheet of plastic or other air impermeable material, The coating completely coats the tube 102 material except in the areas in which heated air is to be exhausted. The uncoated areas form the exhaust ports 212 because air escapes from the tube 102 in those areas. Those skilled in the art will recognize that size, number, and location of the exhaust ports 212 are dependent upon the available air flow.

The exhaust ports 212 cover the surface of the tube 102 in the area in which heated air is desired to be exhausted. In the illustrated embodiment, the tube 102 does not discharge heated air in the area where the patient's ears would be located. The area between exhaust ports 212a and 212b, 212c and 212d is the area of the tube 102 that is adjacent to the ears of the patient 110.

Figure 3:
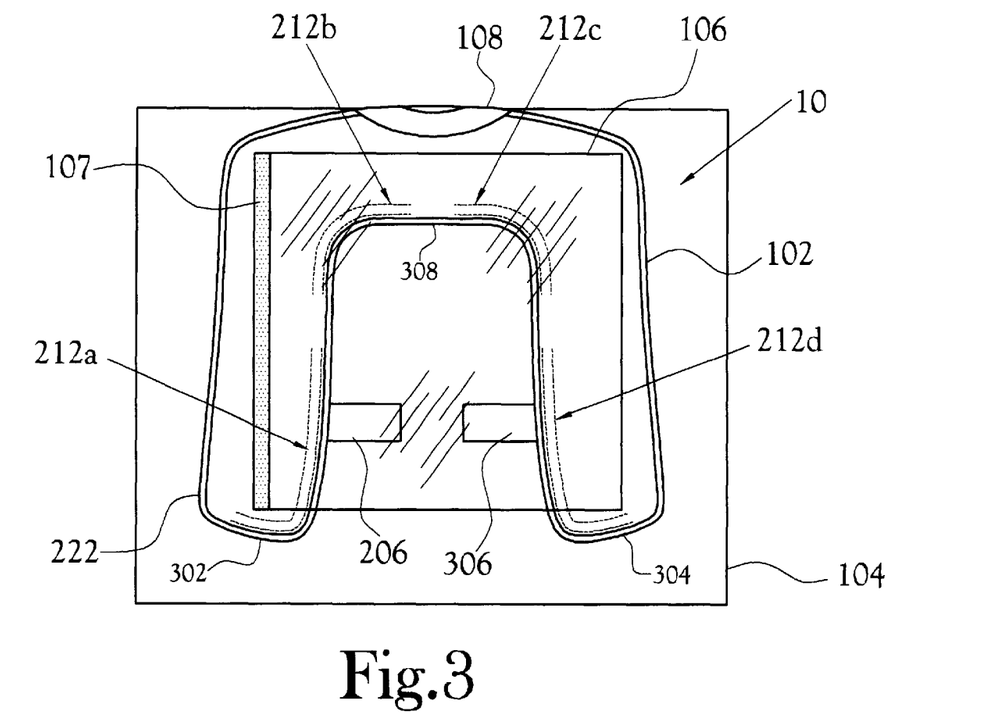
FIG. 3 is a top view of the therapy device.

FIG. 3 shows a therapy device 10 in a deflated state. The legs 302, 304 of the therapy device 10 are splayed out because, when the tube 102 is inflated, the end of the legs 302, 304 draw towards each other. In the illustrated embodiment, the legs 302, 304 are substantially parallel to each other when the therapy device 10 is inflated.

Figure 4:
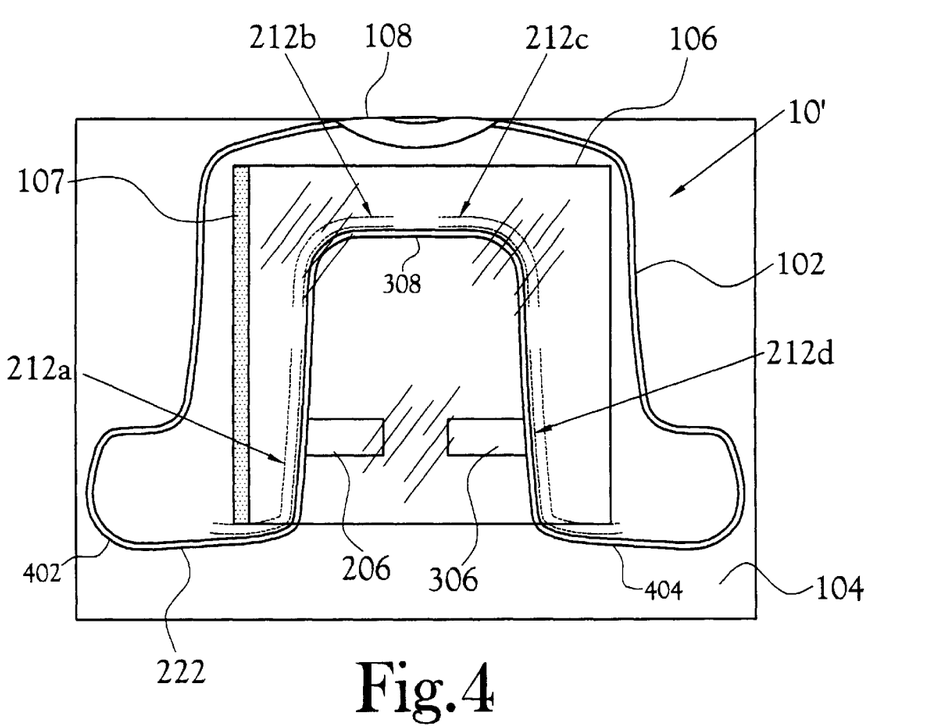
FIG. 4 is a top view of another embodiment of the therapy device.

FIG. 4 shows another embodiment of a therapy device 10' in a deflated state. In this embodiment, the legs 402, 404 of the therapy device 10' have a foot-shaped end portion opposite their connection to the crosspiece 308. The shape of the legs 402, 404 permits the heated air exhausted from the therapy device 10' to be directed across the top of the full width of the shoulders of the patient 110.

Figure 5:
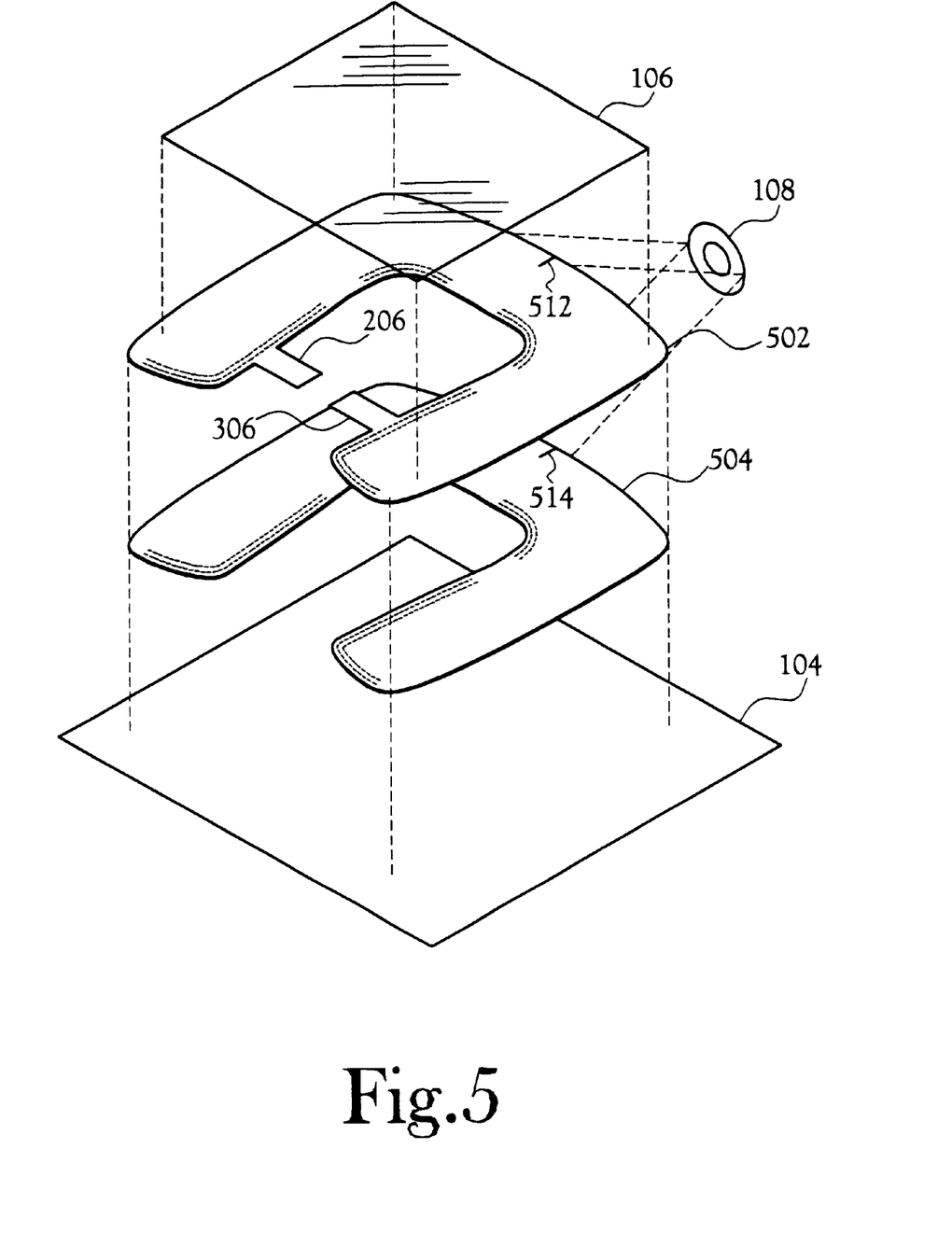
FIG. 5 is an exploded view of the therapy device.
Figure 13:
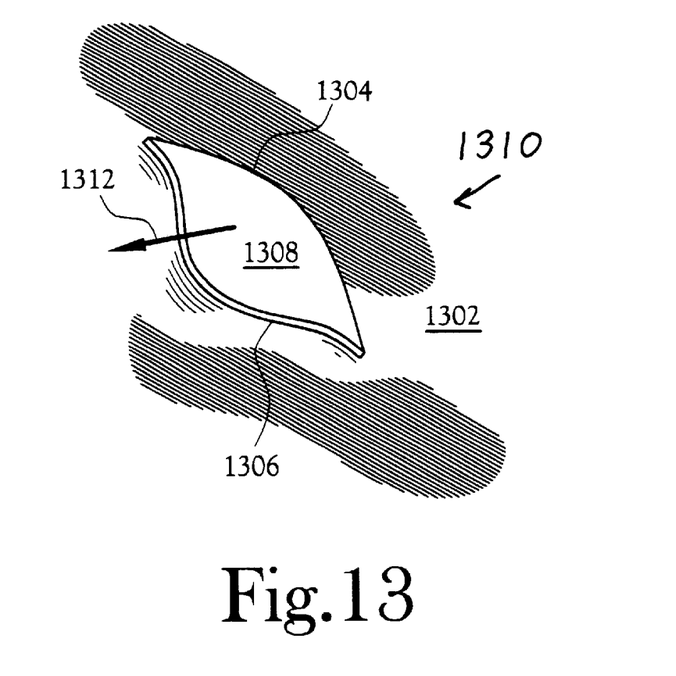
FIG. 13 is a perspective view of a triangular slit.

FIG. 5 is an exploded view of the therapy device 10, showing the base sheet 104, two tube sheets 502, 504, the cover sheet 106, and the inlet collar 108. The base sheet 104 is fabricated of the same material as the tube sheets 502, 504, although those skilled in the art will recognize that other material can be used without departing from the spirit and scope of the present invention. The cover sheet 106 is fabricated of a thin-gauge clear plastic that is impermeable to air, for example, 10 gauge clear PVC sheeting. Although FIG. 13 illustrates straight slits 1310, in one embodiment, the exhaust ports 212 are V-shaped slits 1210, as illustrated in FIG. 12.

The tube 102 is made of two tube sheets 502, 504, one on top of the other. The tube sheets 502, 504 are fabricated of a material that is not permeable to air, such as a fabric coated with a plastic. Those skilled in the art will recognize that any of various materials can be used without departing from the spirit and scope of the present invention. Common materials include woven and non-woven fabrics and cellulosics. Material that is air permeable can be coated on at least one side with a thin film of plastic or other air impermeable material. The material is waterproof and impermeable to air.

In the illustrated embodiment, at least one of the tube sheets 502, 504 has two securing straps 206, 306, each extending from a leg 206, 306 towards the other. In another embodiment, the securing straps 206, 306 are separate pieces of material placed between and secured to the tube sheets 502, 504. The two tube sheets 504, 504 are sealed together at their common edges 222. The sheets 502, 504 can be sealed by gluing the opposing surfaces or by welding the plastic coated surfaces. The sealed edge 222 extends into the tube sheet 502, 504 a distance sufficient to provide an air tight seal and provide mechanical strength when the tube 102 is inflated. For fabric with a plastic film, the sealed distance is approximately one-quarter inch.

In the illustrated embodiment, the tube 102 is secured to the base sheet 104 in four places. The tube 102 is attached by securing the seam 222 on both sides of the inlet collar 108 to the base sheet 104. The tube 102 can be glued or welded to the base sheet 104. The tube 102 is secured to the base sheet 104 by the two securing tabs 206, 306 protruding from the tube 102. Each securing tab 206, 306 is folded under its respective tube leg 302, 304 and secured to the base sheet 104.

The inlet collar 108 is secured to the cross-piece of the tube 102. The inlet collar 108 is a section of stiff material, such as paper or cardboard, with a hole in the center sized to accept the nozzle of the heated air supply hose 112. The inlet collar 108 is attached to the tube sheets 502, 504 by gluing it to the fabric. Slits 512, 514 are cut into the tube sheets 502, 504 and provide clearance for the nozzle of the heated air supply hose 112. In the illustrated embodiment, the inlet collar 108 is not secured to the base sheet 104.

Figure 6:
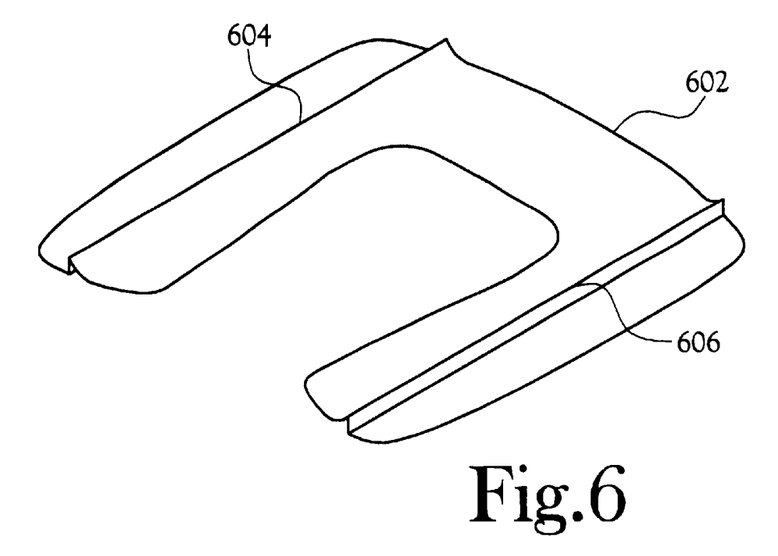
FIG. 6 is a perspective view of one panel of one embodiment the device.
Figure 7:
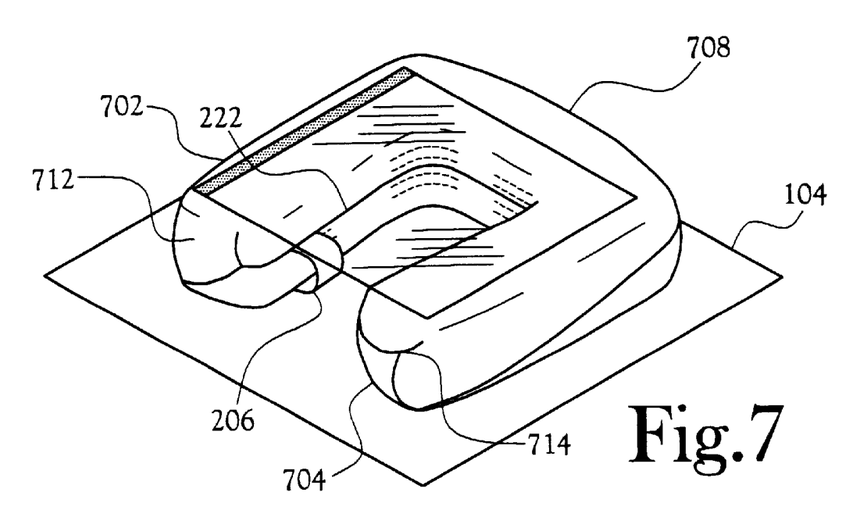
FIG. 7 is a perspective view of the embodiment illustrated in FIG. 6.

FIG. 6 illustrates a tube sheet 602 for another embodiment of the present invention, which is illustrated in FIG. 7. The tube sheet 602, instead of being laid flat during fabrication, has excess material 604, 606 which is folded over along the length of each leg 302, 304. After the tube sheet 602 is attached to its mating tube sheet 504, the tube legs 702, 704 have a greater height than without using the excess material 604, 606. The excess material 604, 606 at the end of the tube legs 702, 704 can be seen in FIG. 7 as a puckered area 712, 714 at the seam 222. As can be seen in FIG. 7, with the upper tube sheet 602 having excess material 604, 606, the seam 222 on the outside of the tube legs 702, 704 is positioned closer to the base sheet 104 at the end of the tube leg 702, 704 opposite the connection to the crosspiece 708. In another embodiment, both the top and bottom tube sheets 502, 504 are similar to the tube sheet 602 with excess material 604, 606. A tube fabricated with excess material 604, 606 on both the top and bottom tube sheet 502, 504 has legs 702, 704 with a greater height, which results in the cover sheet 106 being supported more by the tube legs 702, 704 than the face of the patient 110. Although FIG. 7 illustrates straight slits 1310, in one embodiment, the exhaust ports 212 are V-shaped slits 1210, as illustrated in FIG. 12.

Figure 8:
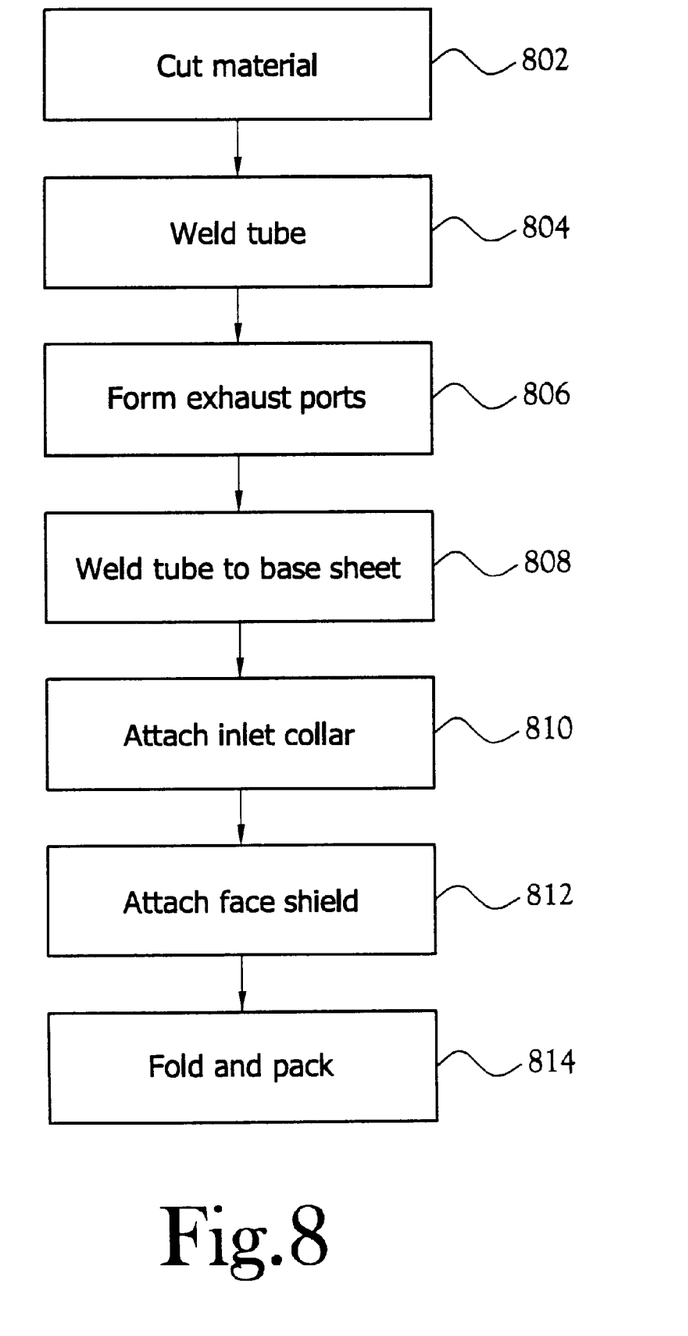
FIG. 8 is a block diagram of the fabrication method steps.

FIG. 8 is a flow diagram showing the steps of fabricating the therapy device 10. The first step is to cut the material 802. Once the material is cut, the tube sheets 502, 504 can be sealed at their common edges 222 by welding 804 or other means for making an air tight seal.

In one embodiment, the exhaust ports 212 are slits 1310 cut parallel to the edge 222 of the tube sheet 502, 504. Once the two tube sheets 502, 504 are fastened together, the exhaust ports 212 are formed 806 by cutting into the material of the tube 102. The exhaust ports 212 can be cut 806 by lancing slits 1210 and 1310 or punching holes in the tube sheets 502, 504. In another embodiment, the exhaust ports 212 are uncoated areas of an air permeable material that is partially coated with a thin film of plastic or other air impermeable material. For this embodiment, when the tube sheet 502, 504 material is coated before cutting, the exhaust ports 212 can be formed 806 before the material is cut. Those skilled in the art will recognize that the number of exhaust ports 212 can vary based on their size and the available air supply flow without departing from the spirit and scope of the present invention.

After the tube sheets 502, 504 are mated 804, the tube 102 is secured to the base sheet 104 by attaching the crosspiece 308 of the tube 102 to the base sheet 104 and by attaching the securing straps 206, 306 to the base sheet 104. The inlet collar 108 is secured 810 to the tube 102 and the cover sheet 106 is attached 812 to the tube 102. Lastly, the assembled therapy device is folded and packed 814, and otherwise made ready for shipment, storage, and use.

In the illustrated embodiment, the patient 110 is positioned on the base sheet 104 with the head of the patient 110 between the legs 302, 304 of the therapy device 10. Heated air is pumped into the therapy device 10 and is exhausted from the exhaust ports 212, which are of a size and number to maintain a back pressure in the therapy device 10, which serves to keep the tube 102 inflated. The cover sheet 106 is extended from one tube leg 302, over the face of the patient 110, and to the other tube leg 304. The therapy device 10 disclosed is suitable for use with a patient 110 off-pump.

Figure 9:
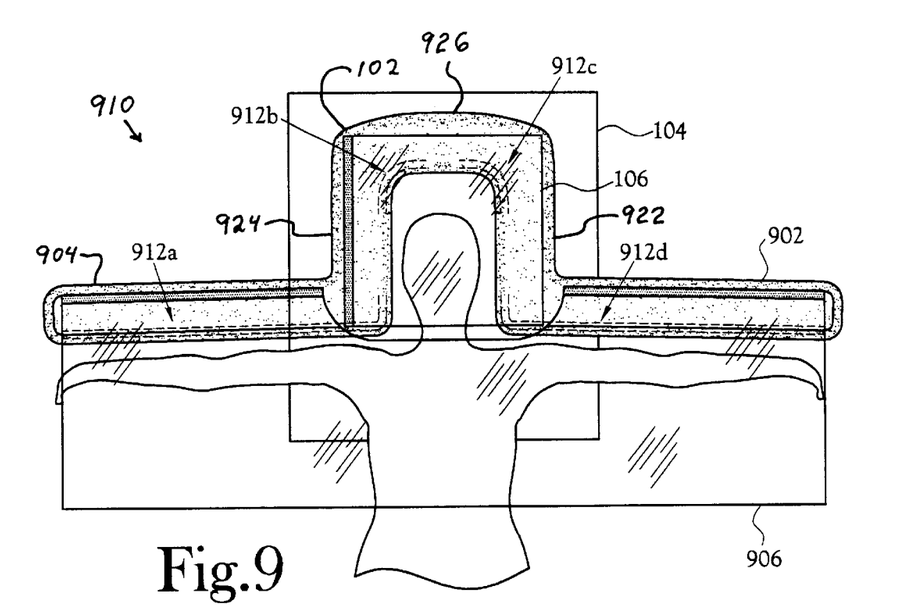
FIG. 9 is a top view of a patient with an inflated therapy device having extended arms.

FIG. 9 is a top view of a patient surrounded by an inflated therapy device 910 having extended arms 902 and 904. The illustrated embodiment of the therapy device has a tube 102 including a crosspiece 926 attached to two legs 922 and 924, attached to an extended foot 902 and 904. The tube 102 is attached to a base sheet 104, and attached to the tube is a head cover sheet 106 and an upper-body cover sheet 906. The cover sheets 106 and 906 contain the warm air that is exhausted through an exhaust region 912a, 912b, 912c, and 912d of the tube 102. The exhaust region 912, in one embodiment, includes a series of straight slits 1310 cut or lanced into the material of the tube 102. In another embodiment, the exhaust region 912 includes a series of V-shaped slits 1210 cut or lanced into the material of the tube 102.

Figure 10:
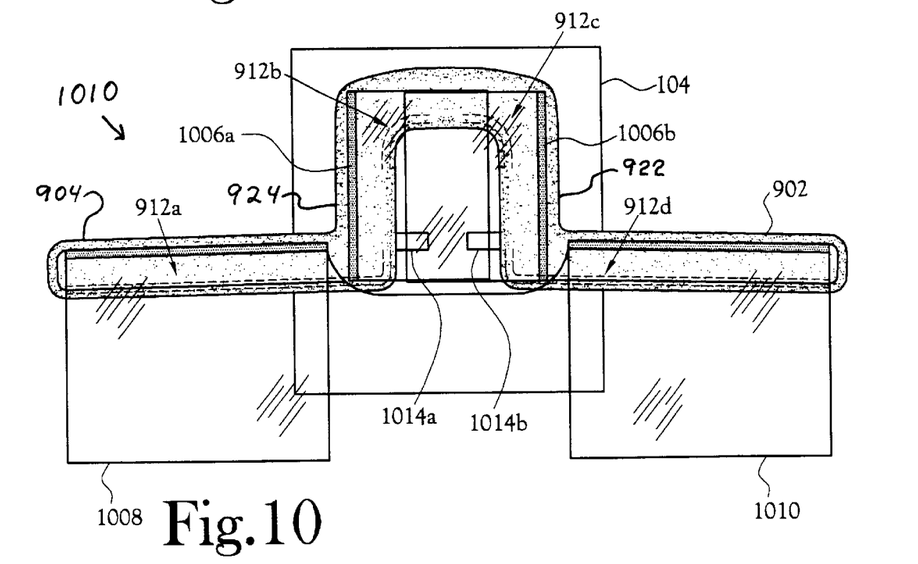
FIG. 10 is a top view of the therapy device having extended arms.

FIG. 10 is a top view of another embodiment of the therapy device 1010 having extended arms 902 and 904. Overlapping head cover sheets 1006a and 1006b are positioned for covering the face of the patient 110. A pair of upper-body cover sheets 1008a and 1008b are positioned for covering the arms of the patient 110, thereby allowing access to the chest of the patient 110. The securing straps 1014A and 1014b attach the tube legs 922 and 924 to the base sheet 104.

Figure 11A:
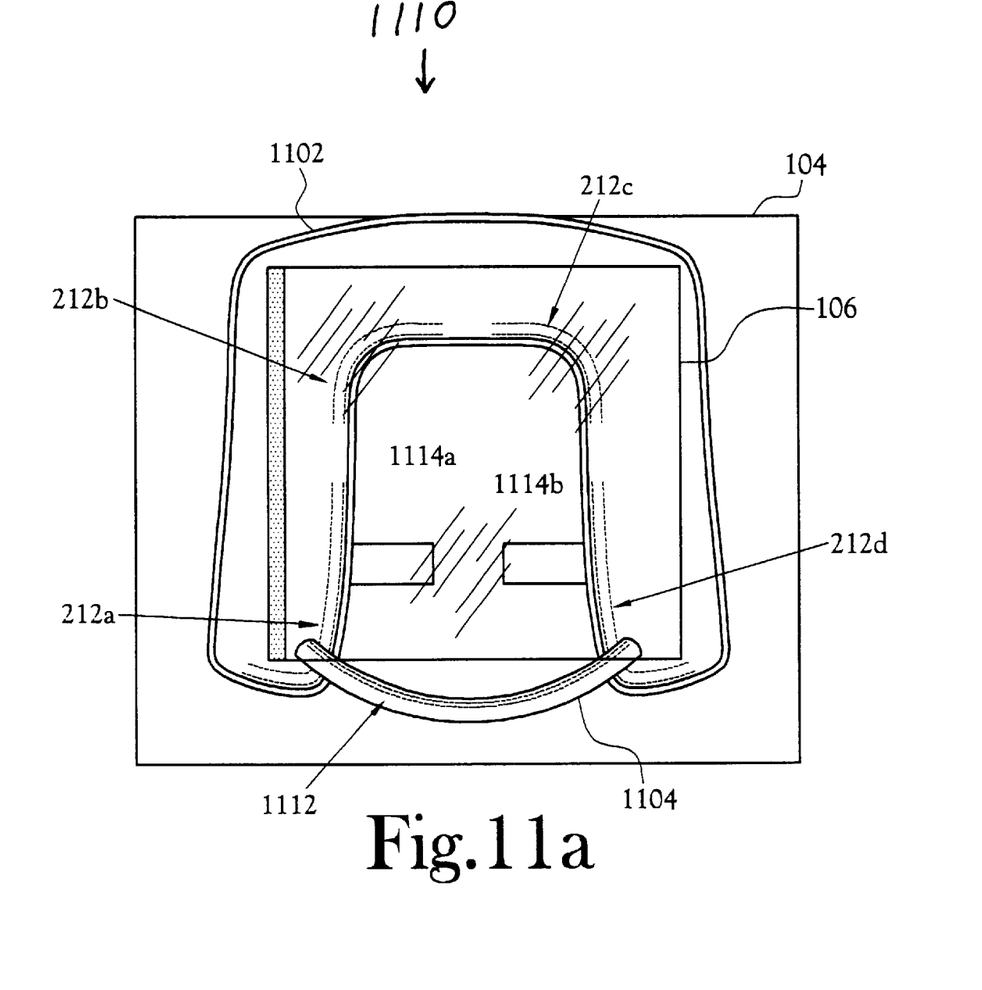
FIG. 11a is a top view of a therapy device with a second crosspiece.

FIG. 11a is a top view of an embodiment of a therapy device 1110 with a second crosspiece 1104. The second crosspiece 1104 has an exhaust region 1112, through which heated air can be directed towards the bottom portion of the head of the patient 110. The exhaust region 1112, in one embodiment, includes a series of straight slits 1310 cut or lanced into the material of the tube 102. In another embodiment, the exhaust region 1112 includes a series of V-shaped slits 1210 cut or lanced into the material of the tube 102. Each end of the crosspiece 1104 is pneumatically connected to the tube 102. In another embodiment, one end of the crosspiece 1104 is pneumatically connected to the tube 102, and the other end of the crosspiece 1104 is closed.

Figure 11B:
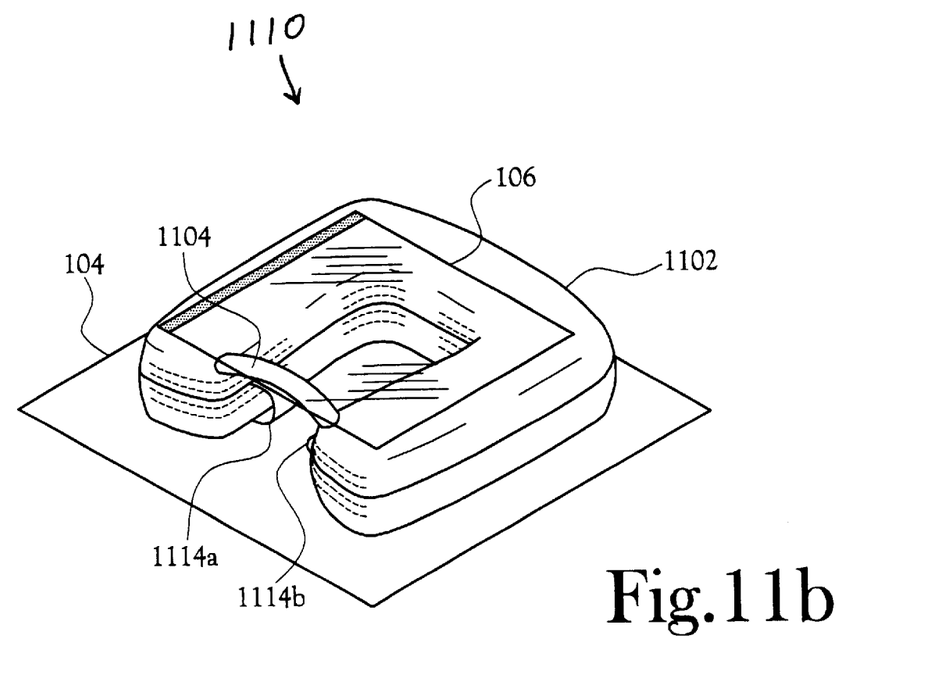
FIG. 11b is a perspective view of the therapy device with a second crosspiece.

FIG. 11b is a perspective view of the therapy device 1110 with the second crosspiece 1104. The crosspiece 1104 is covered by the cover sheet 106, thereby ensuring that the air exhausted by the crosspiece 1104 is contained about the head of the patient 110.

FIG. 12 is a perspective view of a triangular, or V-shaped, slit 1210, which, in one embodiment, forms one of the exhaust ports in the exhaust region 212, 912, 1112, and 1412. The material 1202 of one of the sheets forming the therapy device 10, 910, 1010, 1110, 1410 is cut or lanced in a V-shape, resulting in a V-shaped flap 1204 and an opening 1206. The escaping air 1212 from the therapy device forces the end of the flap 1204 to lift, allowing the air to exhaust through the opening 1206.

Each V-shaped slit 1210 is formed of two straight slits, or cuts, forming an acute angle relative to each other and that are joined at one end. The point of the V-shaped slit 1210 forms a beak 1214 that is not attached to the sheet material 1202. The beak 1214 is free to lift away from the sheet material 1202 when the internal air pressure is greater than the outside air pressure, as when the therapy device 10, 910, 1010, 1110, 1410 is inflated. In one embodiment, the beak 1214 of each V-shaped slit 1210 is directed and points towards the seam or joint of the two sheets 502, 504, 1602, 1604 making up the therapy device 10, 910, 1010, 1110, 1410. In another embodiment, the beak 1214 is directed toward along the normal circumference of the tube 102 at the point where the slit 1210 is located.

FIG. 13 is a perspective view of a straight slit 1310, which, in one embodiment, forms one of the exhaust ports in the exhaust region 212, 912, 1112, and 1412. The material 1302 of one of the sheets forming the therapy device 10, 910, 1010, 1110, 1410 is cut or lanced, forming a slit 1308 with two edges 1304 and 1306. The two edges 1304 and 1306 separate when the therapy device is inflated, allowing the escaping air 1312 to exhaust through the opening 1308. The slit 1310 is cut parallel to the longitudinal axis of the tube 102, that is, the length of the slit 1310 is perpendicular to a line tangent to the circumference of the tube 102. This orientation helps to separate the edges 1304 and 1306 when the tube 102 inflates.

Figure 14:
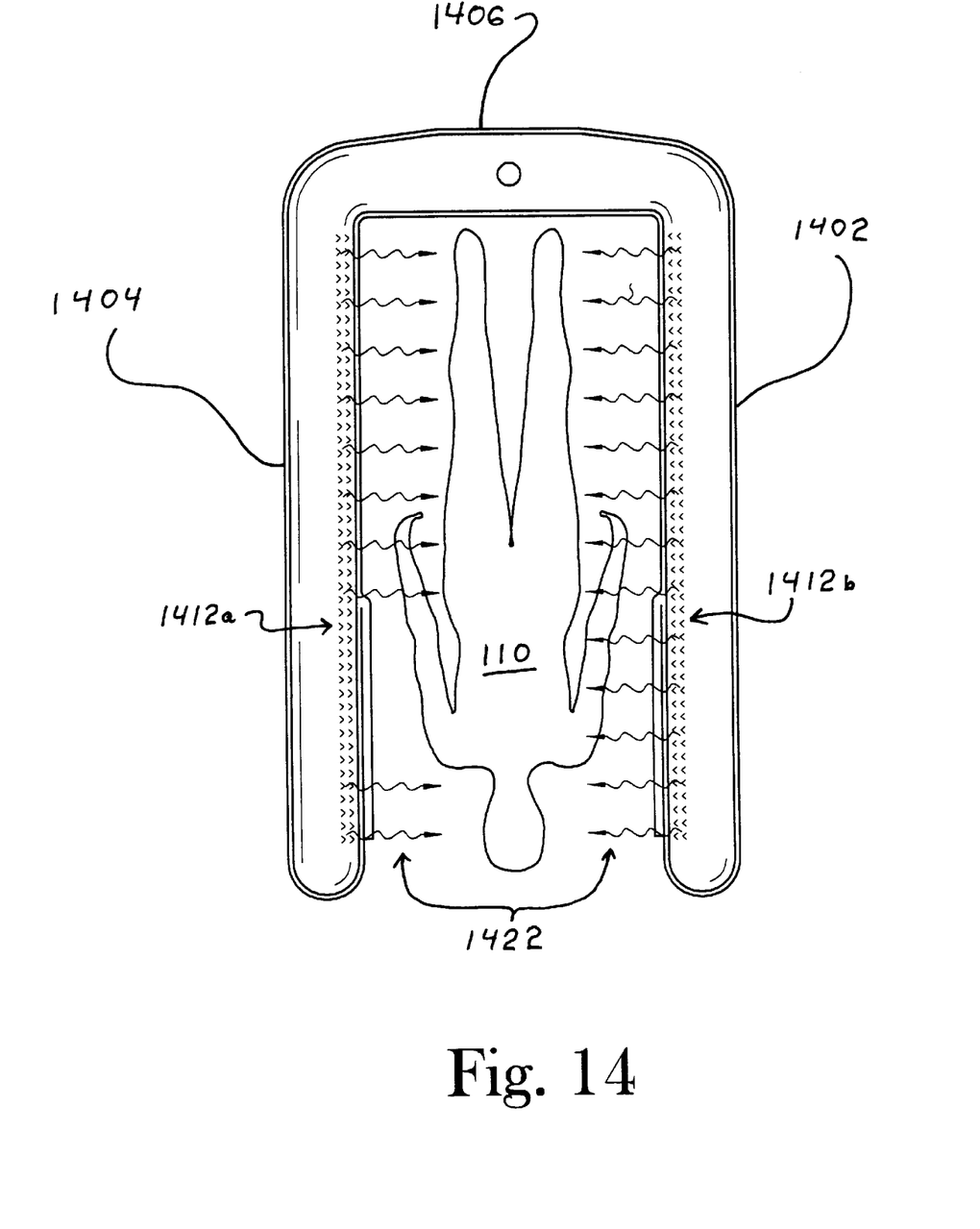
FIG. 14 is a top view of a patient with a full-body therapy device.

FIG. 14 is a top view of a patient with an inflated full body therapy device 1410. The therapy device 1410 has a crosspiece 1406 separating the two tubular legs 1402 and 1404 such that the patient 110 fits between the legs 1402 and 1404. In the illustrated embodiment, the device legs 1402 and 1404 extend the full length of the patient 110. In another embodiment, the device legs 1402 and 1404 extend along a partial length of the patient 110. The crosspiece 1406 includes an inlet port into which heated air is pumped into the therapy device 1410. FIG. 14 illustrates the heated air 1422 leaving the device legs 1402 and 1404 from an exhaust region 1412 and directed towards the patient 110. To keep the air from escaping the area of the body, a flat sheet or blanket (not illustrated) is placed over the therapy device 1410 and the patient 110. The exhaust region 1412, in one embodiment, includes a series of straight slits 1310 cut or lanced into the material of the tube 102. In another embodiment, the exhaust region 1412 includes a series of V-shaped slits 1210 cut or lanced into the material of the tube 102.

Figure 15:
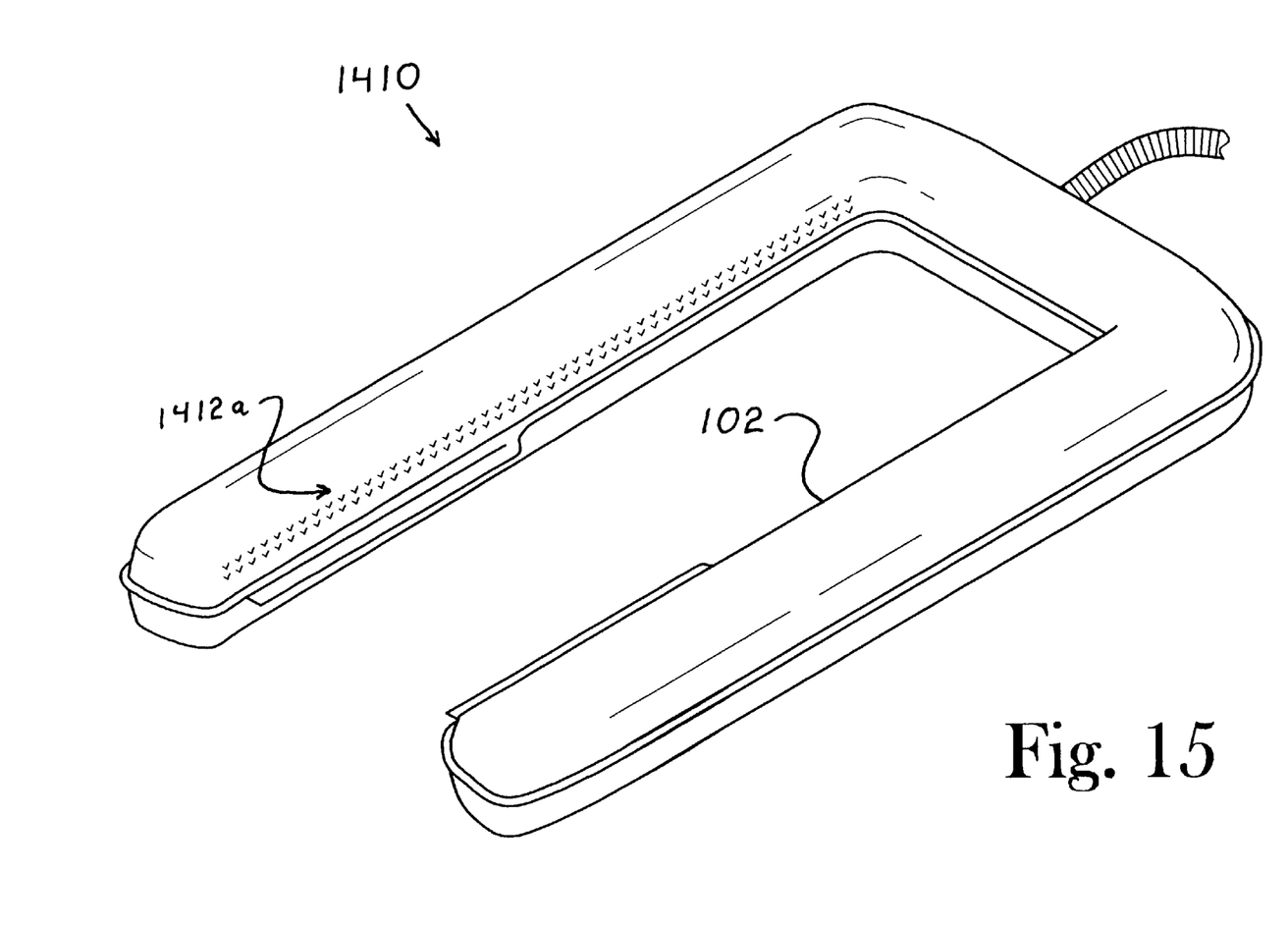
FIG. 15 is a perspective view of an inflated full-body therapy device.

FIG. 15 is a perspective view of the inflated full body therapy device 1410. The illustrated embodiment shows the placement of the exhaust ports 1412a relative to the inside of the U-shaped therapy device 1410. The illustrated embodiment of the therapy device 1410 is formed of two flat sheets 1602 and 1604, in a manner illustrated in FIG. 16.

Figure 16:
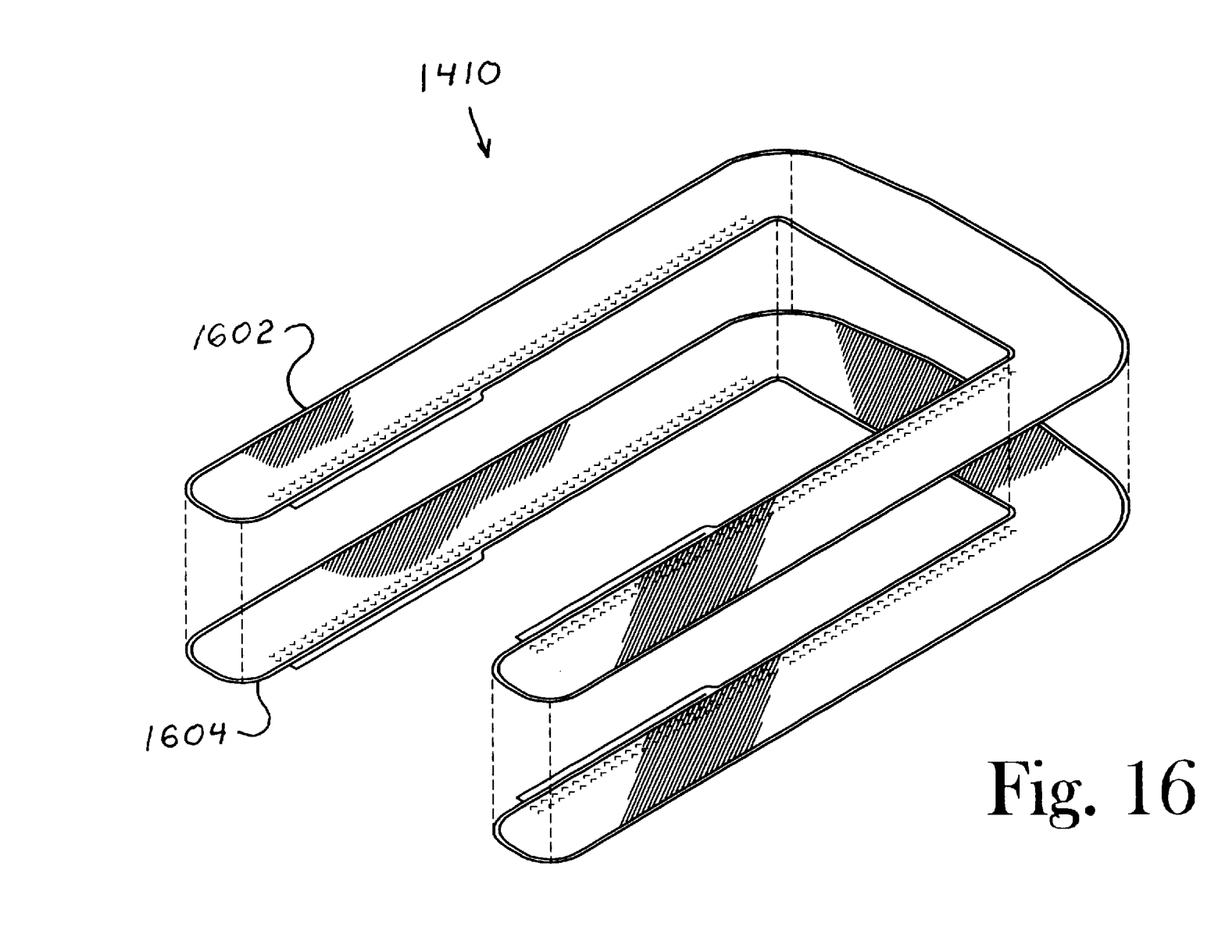
FIG. 16 is an exploded view of the full-body therapy device.

FIG. 16 is an exploded view of the full body therapy device 1410. A first sheet 1602 and a second sheet 1614 of similar size and configuration form the U-shaped tube 102. In one embodiment, an inlet port is attached to the tube 102 in the same manner as illustrated in FIG. 5. In another embodiment (not illustrated), an inlet port is formed in the top sheet 1602. The two sheets 1602 and 1604 are attached at a peripheral edge to form an air impermeable joint such that, when inflated, the two 1602 and 1604 form a tube 102.

From the forgoing description, it will be recognized by those skilled in the art that a therapy device for providing heated air to the upper body of a patient and a method of making the therapy device have been provided. The therapy device is an inflatable U-shaped tube mounted on a base sheet and having a cover sheet. The patient is placed on the base sheet with the patient's head between the legs of the tube. The cover sheet is placed over the patient's face. A heated air supply tube is connected to the tube and the heated air both inflates the tube and is forced out of the exhaust ports of the tube, thereby providing an environment in which a portion of the patient's body is heated.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A therapy device for providing air to a patient's body, said device comprising:
    a first sheet having a first leg, a second leg, a crosspiece, and a first sheet peripheral edge;
    a second sheet having a shape and configuration congruent to that of said first sheet, said second sheet having a second sheet peripheral edge attached to said first sheet peripheral edge and forming an air tight seal between said first sheet and said second sheet, said first sheet and said second sheet defining a tube;
    an inlet port in said tube for forcing air into said tube;
    an air impermeable region defined on a surface of said tube; and
    an exhaust region defined on said surface of said tube, said exhaust region directing air towards the patient's body; and
    a plurality of pairs of straight slits formed in said exhaust region, each of said pair of straight slits connected at a first end and separated at an opposite second end, said pair of straight slits defining a V-shape.

2. The device of claim 1 wherein each of said plurality of pairs of straight slits includes a beak that points toward said first sheet peripheral edge.

3. The device of claim 1 wherein said plurality of pairs of straight slits are located adjacent to said first sheet peripheral edge.

4. A therapy device for providing air to a patient's body, said device comprising:
    a first sheet having a first leg, a second leg, a crosspiece, and a first sheet peripheral edge;
    a second sheet having a shape and configuration congruent to that of said first sheet, said second sheet having a second sheet peripheral edge attached to said first sheet peripheral edge and forming an air tight seal between said first sheet and said second sheet, said first sheet and said second sheet defining a tube;
    an inlet port in said tube for forcing air into said tube;
    an air impermeable region defined on a surface of said tube; and
    an exhaust region defined on said surface of said tube, said exhaust region directing air towards the patient's body; and
    a plurality of pairs of straight slits formed in said exhaust region, each of said pair of straight slits connected at a first end and separated at an opposite second end, said pair of straight slits defining a V-shape having a beak that points toward said first sheet peripheral edge, said plurality of pairs of straight slits are located adjacent to said first sheet peripheral edge.

5. A therapy device for providing air to a patient's body, said device comprising:
    a first sheet having a first leg, a second leg, a crosspiece, and a first sheet peripheral edge;
    a second sheet having a shape and configuration congruent to that of said first sheet, said second sheet having a second sheet peripheral edge attached to said first sheet peripheral edge and forming an air tight seal between said first sheet and said second sheet, said first sheet and said second sheet defining a tube;
    an inlet port in said tube for forcing air into said tube;
    an air impermeable region defined on a surface of said tube; and
    an exhaust region defined on said surface of said tube, said exhaust region directing air towards the patient's body; and
    a means for exhausting air from said tube through V-shaped slits.

6. A therapy device for providing air to a patient's body, said device comprising:
    a means for releasably containing a first quantity of a medium;
    a means for connecting a source of said first quantity of said medium to said means for containing; and
    a means for exhausting a second quantity of said medium from said means for containing through V-shaped slits.

7. A therapy device for providing air to a patient's body, said device comprising:
    a first sheet having a first leg, a second leg, a crosspiece, and a first sheet peripheral edge;
    a second sheet having a shape and configuration congruent to that of said first sheet, said second sheet having a second sheet peripheral edge attached to said first sheet peripheral edge and forming an air tight seal between said first sheet and said second sheet;

an inlet port in said tube for forcing air into said tube;

an air impermeable region defined on a surface of said tube; and an exhaust region defined on said surface of said tube, said exhaust region directing air towards the patient's body; and a plurality of orifices formed in said exhaust region, each of said orifices formed by a single pair of straight slits connected at a first end and separated at an opposite second end, said pair of straight slits defining a V-shape.

8. A therapy device for providing air to a patient's body, said device comprising:

a first sheet having a first leg, a second leg, a crosspiece, and a first sheet peripheral edge;

a second sheet having a shape and configuration congruent to that of said first sheet, said second sheet having a second sheet peripheral edge attached to said first sheet peripheral edge and forming an air tight seal between said first sheet and said second sheet;

an inlet port in said tube for forcing air into said tube;

an air impermeable region defined on a surface of said tube; and an exhaust region defined on said surface of said tube, said exhaust region directing air towards the patient's body; and a plurality of orifices formed in said exhaust region, each of said orifices formed by a pair of straight slits connected at a first end and separated at an opposite second end, said pair of straight slits defining a V-shape having a beak that points toward said first sheet peripheral edge, said plurality of pairs of straight slits located adjacent to said first sheet peripheral edge.

* * * * *